(12) United States Patent
Verburg et al.

(10) Patent No.: US 10,031,347 B2
(45) Date of Patent: Jul. 24, 2018

(54) MULTIFOCAL OPHTHALMIC LENS TO BE WORN IN OR ON THE EYE

(71) Applicant: Ophtec B.V., Groningen (NL)

(72) Inventors: Erik Verburg, Groningen (NL); Peter Biemold, Groningen (NL); Alfred Willem Wassenburg, Groningen (NL)

(73) Assignee: Ophtec B.V., Groningen (NL)

(*) Notice: Subject to any disclaimer, the term of this patent is extended or adjusted under 35 U.S.C. 154(b) by 0 days.

(21) Appl. No.: 15/115,358

(22) PCT Filed: Feb. 2, 2015

(86) PCT No.: PCT/NL2015/050067
§ 371 (c)(1),
(2) Date: Jul. 29, 2016

(87) PCT Pub. No.: WO2015/115901
PCT Pub. Date: Aug. 6, 2015

(65) Prior Publication Data
US 2017/0010477 A1    Jan. 12, 2017

(30) Foreign Application Priority Data

Jan. 31, 2014 (EP) .................................... 14153523
Jul. 11, 2014 (EP) .................................... 14176734

(51) Int. Cl.
*G02C 7/00* (2006.01)
*G02C 7/02* (2006.01)
(Continued)

(52) U.S. Cl.
CPC ............ *G02C 7/044* (2013.01); *A61F 2/1618* (2013.01); *G02C 7/042* (2013.01); *G02C 7/045* (2013.01)

(58) Field of Classification Search
CPC ........ G02C 7/044; G02C 7/045; G02C 7/042; A61F 2/1618
(Continued)

(56) References Cited

U.S. PATENT DOCUMENTS

| 4,898,461 A | 2/1990 | Portney |
| 4,906,245 A | 3/1990 | Grengahl |

(Continued)

FOREIGN PATENT DOCUMENTS

| CA | 1332491 | 10/1994 |
| EP | 0107444 A2 | 5/1984 |

(Continued)

OTHER PUBLICATIONS

International Search Report issued in connection with PCT/NL2015/050067.

*Primary Examiner* — Tuyen Tra
(74) *Attorney, Agent, or Firm* — Akerman LLP

(57) ABSTRACT

An ophthalmic multifocal lens to be worn on or in a human eye. The lens has an optical portion with anterior and posterior surfaces and a circumferential peripheral boundary. The optical portion has far vision zones having a first refractive power and near vision zones having an add power. The far visions zones and near vision zones include ring segments having one of the refractive powers each radially bounding a more central zone of another one of the refractive powers. The ring segments include ring segments bordering on the peripheral boundary and alternating in circumferential sense along the full circumference of the peripheral boundary.

18 Claims, 5 Drawing Sheets

(51) Int. Cl.
*G02C 7/04* (2006.01)
*A61F 2/16* (2006.01)

(58) Field of Classification Search
USPC .............. 351/159.02, 159.05, 159.1, 159.12, 351/159.13
See application file for complete search history.

(56) References Cited

U.S. PATENT DOCUMENTS

| | | |
|---|---|---|
| 5,173,723 A | 12/1992 | Volk |
| 5,512,220 A | 4/1996 | Roffman et al. |
| 6,986,578 B2 | 1/2006 | Jones |
| 2005/0088615 A1 | 4/2005 | Roffman et al. |

FOREIGN PATENT DOCUMENTS

| | | |
|---|---|---|
| EP | 0858613 B1 | 7/1999 |
| EP | 1176929 B1 | 3/2004 |
| EP | 1712947 A2 | 10/2006 |
| EP | 1212652 B1 | 7/2007 |
| EP | 2219065 A1 | 8/2010 |

MULTIFOCAL OPHTHALMIC LENS TO BE WORN IN OR ON THE EYE

FIELD AND BACKGROUND OF THE INVENTION

This application is a national phase of PCT/NL2015/050067, filed Feb. 2, 2015, and claims priority to EP 14153523.7, filed Jan. 31, 2014, and EP 14176734.3, filed Jul. 11, 2014, the entire contents of all of which are hereby incorporated by reference.

The invention relates to an ophthalmic lens to be worn in or on the eye, such as a contact lens or an intraocular lens, the lens having zones with different refractive optical powers.

Presbyopia is a condition in which, with age, the eye is less able to accommodate for focusing on objects at different distances from the eye by bending the natural lens in the eye. Generally, the ability to change the focal distance between objects far away and nearby declines throughout life, from an accommodation of about 20 diopters (ability to change focal distance between infinity to 50 mm away) in a child, to 10 diopters at age 25 (infinity to 100 mm), and levels off at 0.5 to 1 diopter at age 60 (infinity to 1-2 meters only). The ability to accommodate is also lost if the natural lens is removed, a treatment commonly undergone by cataract patients.

The ability to focus on objects nearby and on objects far away without resorting to changing the focal distance of correction optics, e.g. by using reading glasses or multifocal spectacle lenses, can be improved by using multifocal intraocular lenses or contact lenses. Multifocal lenses have different focal distances for near and far vision. In some lenses, the additional optical power of the near vision is provided by a diffractive pattern at the front or back surface of the lens. Diffractive multifocal lenses suffer from dysphotopsia (blur, glare, halos) and light loss. In other lenses, different focal distances are created by providing zones with different refractive power. Use of such lenses entails loss of contrast caused by the transition zone between the zones for near and far vision. The difference in radius of the zones for near vision and far vision ($R_{nearvision} < R_{farvision}$) results in a step in surface level between the near and far vision zones. In some lenses, it is attempted to design the step to minimize dysphotopsia, for instance by providing a transition zone designed to direct the light which enters the lens through the transition zone to parts in the eye where the light does not disturb vision.

Because in diffractive multifocal lenses the additional optical power is provided by a diffractive structure added to the refractive lens shape, the ratio between amounts of light diffracted and refracted with different focal distances independent of the location of the lens in or on the eye relative to the pupillary area. When a refractive multifocal is not centered relative to (coaxial with) the pupillary area of the eye, the ratio between light passing through a near vision zone and light passing through a far vision tends to change. In other types of multifocal lenses, such as diffractive lenses, an angular difference between the optical axis of the eye and the pupil axis (angle K) can cause patient dissatisfaction due to optical disturbances.

In U.S. Pat. No. 5,512,220 a lens is described in which optical disturbances at junctions between borders between near vision and far vision zones are avoided by having the borders between the near vision and far vision zones in the form of semi-circular paths ending outside the optical region of the lens.

SUMMARY OF THE INVENTION

It is an object of the present invention to provide a lens for improving the ability to focus on objects nearby and on objects far away without resorting to changing the focal distance of correction optics, e.g. by using reading glasses or multifocal spectacle lenses, with reduced dysphotopsia and in particular a high efficiency of directing light to the desired foci of light and a ratio of near and far vision enhancement that remains very constant when pupil size varies and on which lens decentration is of very little influence.

This object is achieved by providing an ophthalmic multifocal lens to be worn on or in a human eye, the lens having an optical portion with anterior and posterior surfaces and a circumferential peripheral boundary, the optical portion having far vision zones having a first refractive power and near vision zones having an add power, the far vision zones and near vision zones including ring segments having one of the refractive powers each radially bounding a more central zone of another one of the refractive powers, the ring segments including ring segments bordering on the peripheral boundary and alternating in circumferential sense along the full circumference of the peripheral boundary.

Because the far vision zones and near vision zones include ring segments each radially bounding a more central zone, the ring segments include far vision ring segment zones and near vision ring segment zones bordering on the peripheral boundary and alternating in circumferential sense along the full circumference of the peripheral boundary, a succession of far and near vision zones in both radial and circumferential sense can be provided without requiring a substantial transition zone in the optical area that deteriorates optical efficiency. In particular, differences in level in the direction of the optical axis between adjacent near and far vision zones are reduced, up to the peripheral boundary, where any remaining step in the transition to the non optical portion is not problematic optically. Since a combination of near and far vision zones in radial direction is provided over most of the optical surface and alternates over the full circumference, the ratio of light reaching the retina via near vision zones and light reaching the retina via far vision zones is very insensitive to pupil size variations and out of center positioning of the lens as occurs in practice.

Particular elaborations and embodiments of the invention are set forth in the dependent claims Further features, effects and details of the invention appear from the detailed description and the drawings.

DETAILED DESCRIPTION

Figure 1:
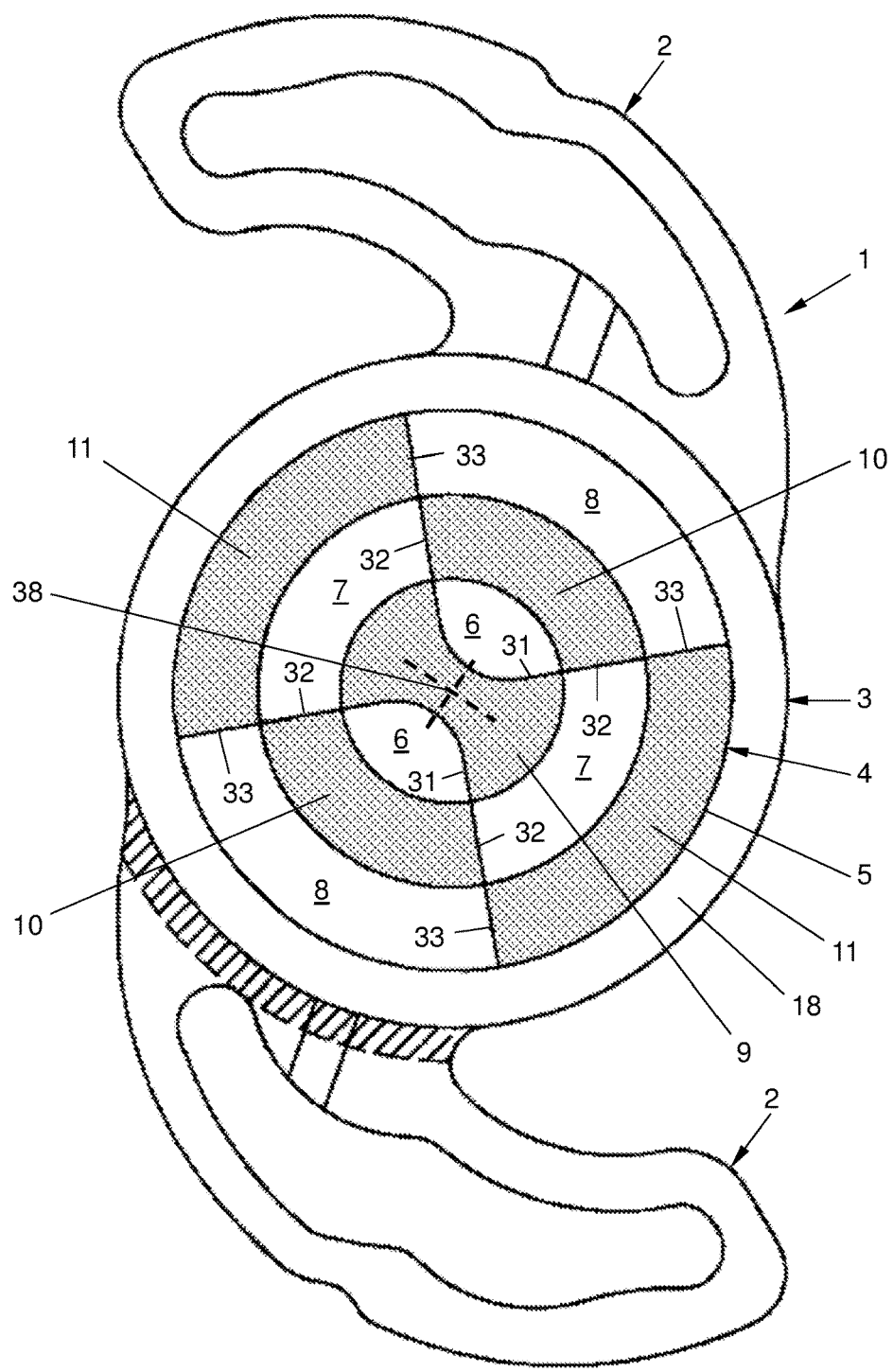
FIG. 1 is a frontal view of a first example of a lens according to the invention.

In FIG. 1 a first example of an ophthalmic multifocal lens according to the invention is shown in the form of an intraocular lens 1 with haptics 2, a lens body 3 and an optical portion 4. The lens 1 according to the present example is designed for implantation in a capsular bag of an aphakic eye (eye from which the natural lens has been removed) and accordingly to be worn in a human eye. Such intraocular lenses generally have an optical portion having a diameter of 5-8 mm, an overall diameter 12-15 mm and are for instance made of PMMA or hydrophilic acrylic, hydrophobic acrylic, silicone, polyurethane or collamer material. Lenses according to the invention may also be provided in other forms to be worn in or on the eye, for instance in the form of a lens to be worn in the anterior chamber of the eye, which allows implantation in an eye having the natural lens in place, or in the form of a contact lens. Anterior chamber intraocular lenses generally have an optical portion having a diameter of 5-8 mm, an overall diameter of 8-15 mm and are for instance made of PMMA or hydrophilic acrylic, hydrophobic acrylic, silicone, polyurethane or collamer material. A contact lens is typically free of haptics and the non optical portion of the lens body peripherally bounding the optical portion will be shaped to provide a smooth transition to the outer surface of the cornea and desired floating and adherence characteristics. Hard contact lenses generally have a diameter of 8-9 mm and are made for instance of PMMA or fluorosilicone acrylate or silicone acrylate material. Soft contact lenses generally have a diameter of 14-14.5 mm and are made for instance of silicone elastomer, silicone-containing macromer, hydrogel or silicone-containing hydrogel material. Generally, a lens according to the invention may for instance have an overall diameter of less than 15 to 16 mm and an optical portion having a diameter of less than 9 to 10 mm.

The optical portion 4 of the lens body 3 is the largest portion of the lens that can be expected to be positioned in or on the eye such that light passing there through reaches the retina in a way contributing to the image projected on the retina. In view of round shape of the pupillary area through which light passes to the retina and the generally random distribution of decentration occurring in practice, the peripheral boundary of the optical portion is typically of a roundish shape, such as circular or oval. In the present example, the peripheral boundary 5 of the optical portion 4 has a circular shape. In the present example, the peripheral boundary 5 moreover coincides with the peripheral boundary of the front and back surfaces of the lens that are shaped for providing optical refraction with a power for improving vision. However, the non-optical portion may also be shaped such that it has a refractive optical power, e.g. as a continuation of at least some zones of the optical portion.

The optical portion 4 has anterior and posterior surfaces shaped such that far vision zones 6, 7, 8 having a first refractive power and near vision zones 9, 10, 11 having an add power are formed. In the drawings, the near vision zones have been shaded, but are equally transparent as the far vision zones. The far vision zones 6, 7, 8 and the near vision zones 9, 10, 11 including ring segments 7, 8, 10, 11 each radially bounding a more central zone 6, 7, 9, 10. The ring segments 7, 8, 10, 11 include ring segments 8, 11 bordering on the peripheral boundary 5. These far vision and near vision ring segments alternate in circumferential sense along the full circumference of the peripheral boundary 5 of the optical portion 4.

Figure 9:
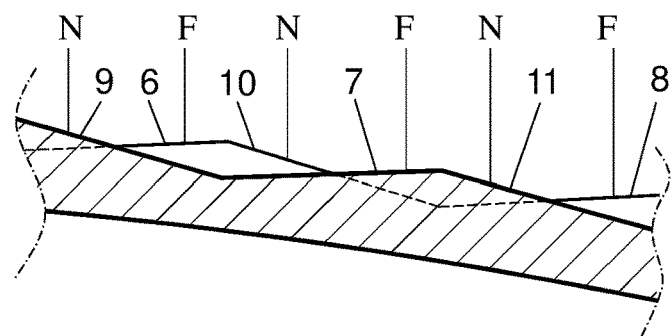
FIG. 9 is a schematic cross sectional view of the lens according to FIG. 1 along a meridian closely along borders between circumferentially adjacent near and far vision zones.

Thus, a succession of far and near vision zones 6-11 in both radial and circumferential sense is provided without requiring a substantial transition zone in the optical area that deteriorates optical efficiency. Border zones forming transitions between adjacent optical zones may for instance cover less than 5%, less than 3% or less than 1% of the surface area of the optical portion. In view of small steps in surface level between circumferentially adjacent zones, this will generally be sufficient for providing a sufficiently smooth transition. In particular, differences in level in the direction of the optical axis between circumferentially adjacent near and far vision zones are reduced, up to the peripheral boundary, because in radial sense an alternation of near and far vision zones is obtained over essentially the full optical portion of the lens. As is illustrated by FIG. 9, the alternation of near vision zones N and far vision zones F in radial sense causes the maximum difference in surface level between circumferentially adjacent near and far vision zones to be relatively small. In the example shown, of a set of circumferentially adjacent ones of the ring segments, a first one is of a thickness varying from a first thickness at a radially inner border of the first ring segment to a second thickness at a radially outer border of the first ring segment and a second one is of a thickness varying from a third thickness at a radially inner border of the second ring segment to a fourth thickness at a radially outer border of the second ring segment. The first thickness is smaller than the third thickness and the second thickness is larger than the fourth thickness and the circumferentially adjacent ring segments of the set are of equal thickness in a position located in radial sense between the inner and outer borders of the set of circumferentially adjacent ring segments. Thus, the varying thicknesses of the circumferentially adjacent ring segments intersect each other so that the maximum difference in surface level between circumferentially adjacent near and far vision ring segment zones 9 and 6, 10 and 7 and 11 and 8 is particularly small.

For reducing differences in surface level between circumferentially adjacent near and far vision ring segment zones over the entire optical portion, this principle may be applied for at least one other set of circumferentially adjacent ones of the ring segments, radially adjacent the set of circumferentially adjacent ones of the ring segments or even for each set of circumferentially adjacent ones of the ring segments.

For reducing the maximum difference in surface level between circumferentially adjacent near and far vision ring segment zones 9 and 6, 10 and 7 and 11 and 8 is particularly small, positions of equal thickness of circumferentially adjacent ones of the ring segments can be located in a zone between for instance 30 and 70% or, for a further reduction, between 40 and 60% of the distance between the inner and outer borders of the respective ring segments.

Any remaining step in the transition to the peripheral non optical portion is not problematic optically. Since a combination of near and far vision zones in radial direction is provided over most of the optical surface and the near and far vision ring segment zones alternate over the full circumference up to the outer peripheral boundary, the ratio of light reaching the retina via near vision zones and light reaching the retina via far vision zones is very insensitive to pupil size variations and out of center positioning of the lens as occurs in practice.

Figure 5:
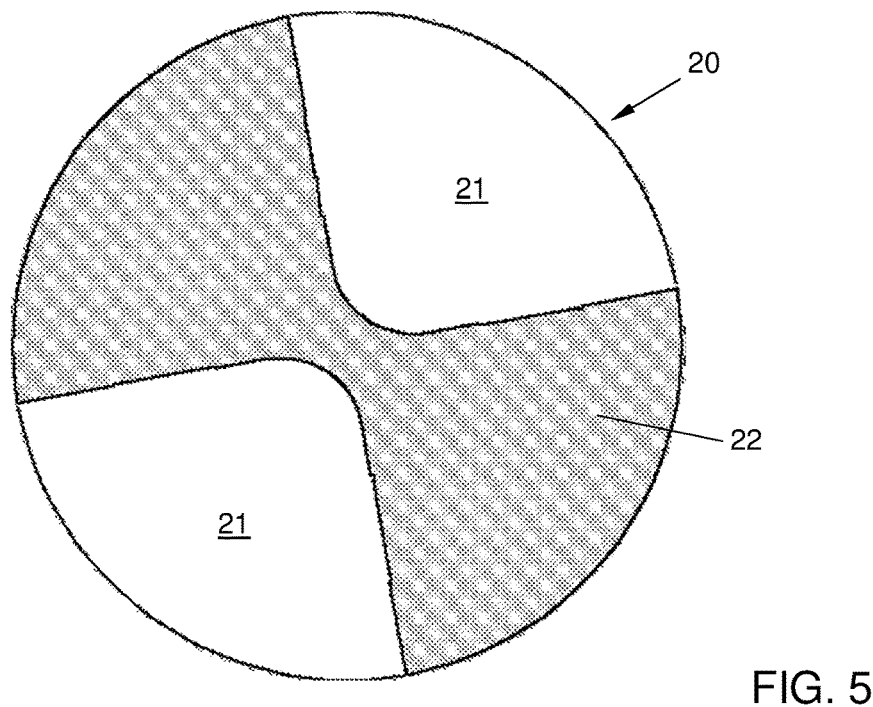
FIG. 5 is a frontal view of an optical portion of an example of a lens not according to the invention.
Figure 6:
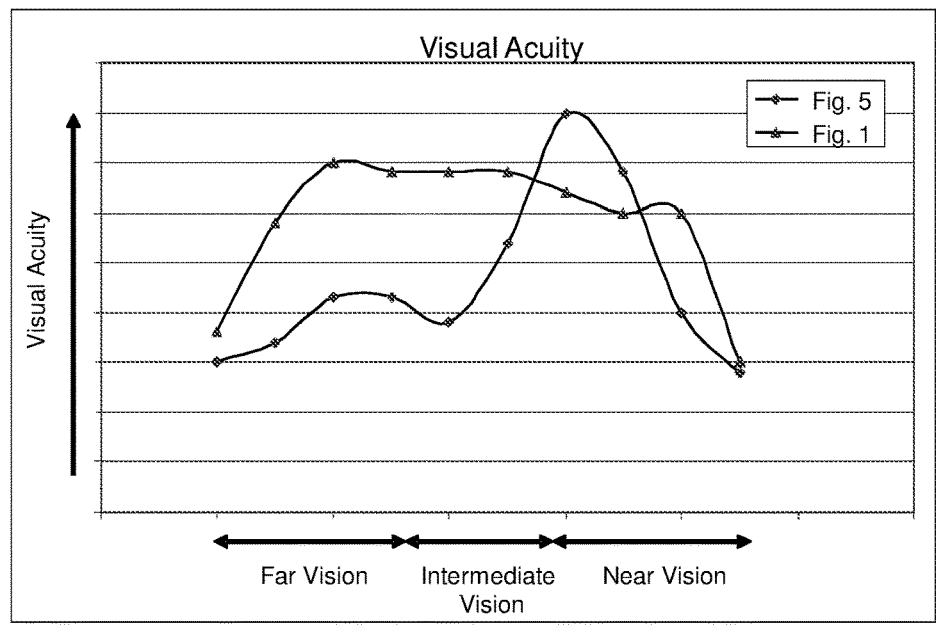
FIG. 6 is a graph showing visual acuity provided by a lens according to the invention as shown in FIG. 1 and visual acuity provided by a lens not according to the invention as shown in FIG. 5.

These optical advantages are illustrated by measurement results comparing a lens as shown in FIG. 1 with a lens not according to the invention of which an optical portion 20 is shown in FIG. 5. This lens has a far vision zone 21 and a near vision zone 22, but the far vision zones and near vision zones 21, 22 do not include ring segments of both refractive powers each radially bounding a more central zone of another one of the refractive powers and the ring far vision and near vision ring segment zones bordering on the peripheral boundary do not alternate in circumferential sense along the full circumference of the peripheral boundary. As is shown in FIG. 6, the lens according to FIG. 1 provides a substantially more constant visual acuity over the far to near distance range than the lens according to FIG. 5. Moreover, compared with the lens according to FIG. 5, the lens according to FIG. 1 provides a substantially better visual acuity in the far to intermediate distance range and in the near distance range and only a somewhat less good visual acuity in a relatively narrow intermediate to near distance range.

In contact lenses, small steps between adjacent visual zones are not only advantageous for optical reasons, but also for improving wear comfort against the cornea or the eye lids, in particular when blinking.

Figure 7:
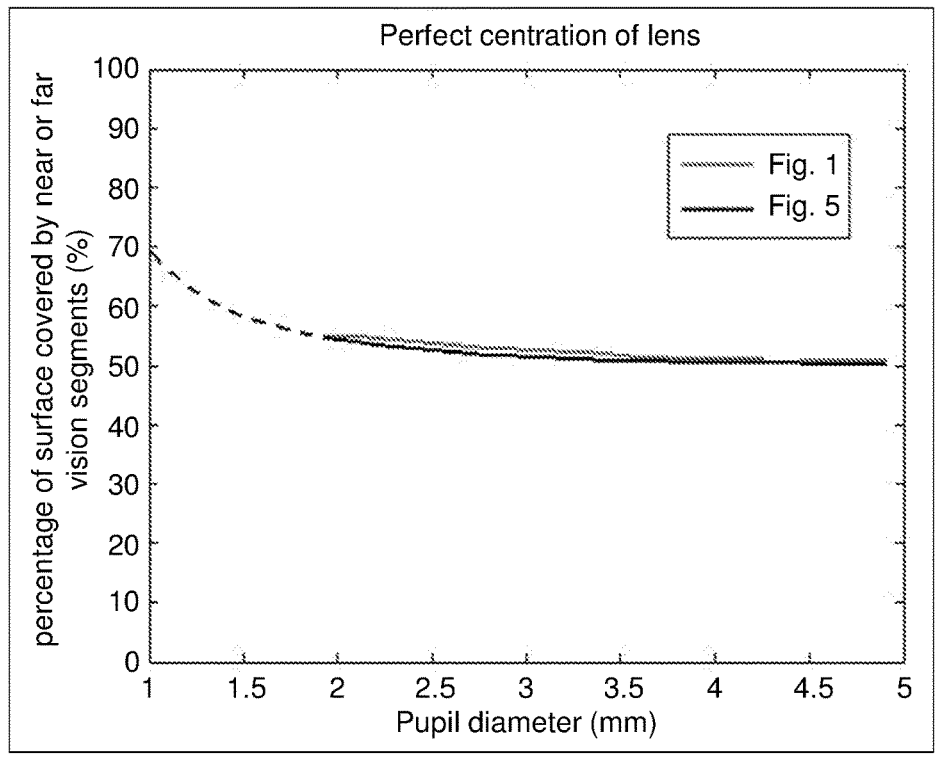
FIG. 7 is a graph showing the effect of pupil size variation on the percentage of optically effective surface area covered by far vision and near vision zones for a lens according to the invention as shown in FIG. 1 and for a lens not according to the invention as shown in FIG. 5, the lenses being perfectly centered.
Figure 8:
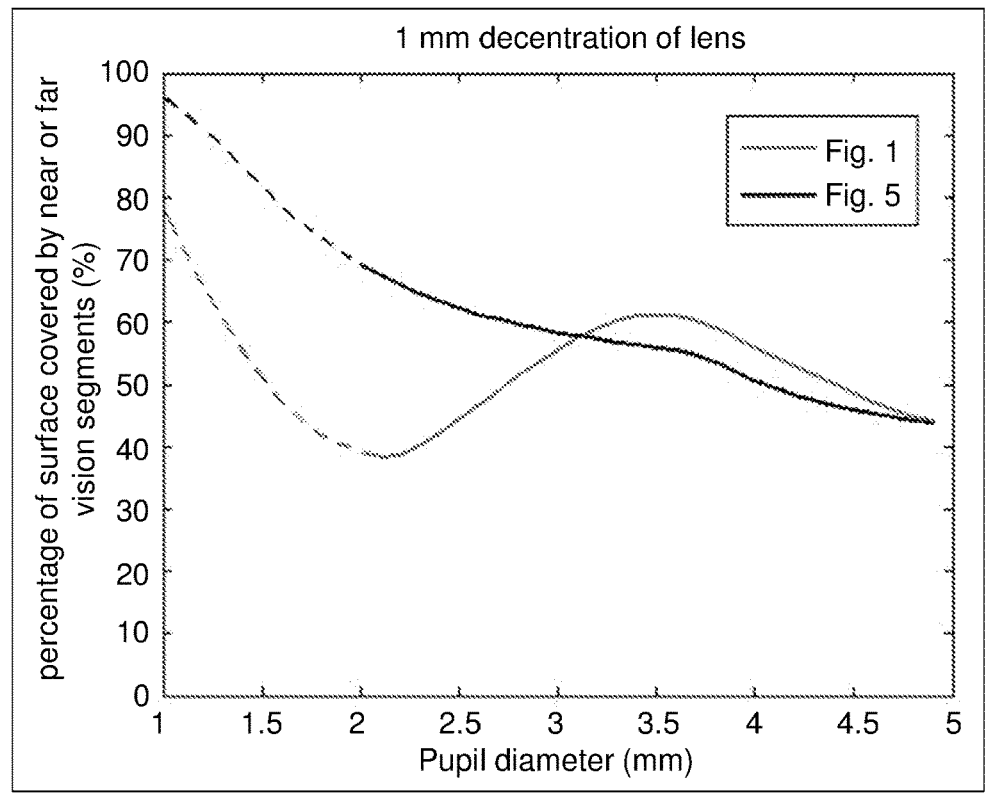
FIG. 8 is a graph showing the effect of pupil size variation on the percentage of optically effective surface area covered by far vision and near vision zones for a lens according to the invention as shown in FIG. 1 and for a lens not according to the invention as shown in FIG. 5, the lenses being 1 mm off center, which is a worst extent of decentration commonly occurring in practice.

FIG. 7 shows that, for a perfectly centered lens, changes in the ratio between optically active surface areas of near and far vision zones due to changes in pupil diameter are about the same and quite limited. However, as is shown in FIG. 8, when looking at a lens with a 1 mm decentration, a worst centration normally encountered in practice, the range in which the ratio between optically active surface areas of near and far vision zones changes due to changes in pupil diameter is larger for the lens not according to the invention than for a lens according to the invention, in which the percentage of the optically active surface area covered by near or far vision zones decrease again after having increased when the pupil diameter decreases from 5 mm to 2 mm.

In the example shown in FIG. 1, the ring segments, 7, 10 in a ring inwardly of the ring segments 8, 11 bordering on the peripheral boundary 5 each bound a radially more central zone 6, 9 along a full inner circumference of that ring. This allows difference in surface level between adjacent near vision and far vision zones, and accordingly optical disturbance, to be reduced.

Furthermore, each far vision one 8 of the ring segments 8, 11 bordering on the circumferential peripheral boundary 5 radially bounds a near vision ring segment 10 of a ring inwardly of the ring segments 8, 11 bordering on the peripheral boundary 5 and each near vision one 11 of the ring segments 8, 11 bordering on the circumferential peripheral boundary 5 radially bounds a far vision ring 7 segment of the ring inwardly of the ring segments 8, 11 bordering on the peripheral boundary. Thus, an alternation between near and far vision zones radially inwardly from the peripheral boundary is achieved over the entire circumference optical portion 4, so that small steps between surfaces of adjacent near and far vision zones can be achieved over the entire circumference optical portion 4.

Borders 31 between most central ones 6, 9 of the near vision and far vision zones are curved with a convex side facing a center 38 of the optical portion 4 and each other, so that intersections of borders between adjacent near and far vision zones in a central portion of the optical portion 4 are avoided. Another advantage of this feature is that manufacturing a lens having borders between near and far vision zones passing through a center of the lens is very difficult and costly. Such a lens is for instance manufactured by turning, in which a lens blank is placed on a rotating machining holder and subjected to the influence of one or more material-removing tools, while the rotating lens or the tool is subjected to a to and fro movement in the direction of the axis of rotation as a function of rotation of the lens to form at least one of elevations, peripheral edge thickening or reading lens.

The borders 31 have continuations 32, 33 extending radially towards the peripheral boundary 5 of the optical portion 4, so that borders 33 between circumferentially neighboring ones 8, 11 of the ring segments bordering on the peripheral boundary 5 are in line with borders 32 between circumferentially neighboring ones 7, 10 of the ring segments of the ring inwardly of the ring segments 8, 11 bordering on the peripheral boundary 5. This reduces the number of intersections of borders, so that optical disturbance is limited. Moreover, steps between successive zones in radial direction can then be kept very small over the entire length of the border between these zones by providing that, ring segments radially bounding a more central zone are flush with the more central zone bounded thereby in at least one position along a border between that ring segment and the more central zone. Each next zone in radial direction can be lifted or lowered to minimize the step between the surface of that zone and the surface of the radially adjacent zone very effectively, because the level of each next vision zone has to be adapted to level one more inward vision zone only. Also if at least the near or far vision zones are of an aspheric shape, a step between radially adjacent near and far vision zones can be mutually, essentially flush over the entire length of the border between these near and far vision zones by applying a surface level correction that is incrementally different for each meridian zone.

While the step between radially adjacent zones can be reduced to zero or almost zero along the entire length of the border between two of such successive zones, the step between circumferentially adjacent near vision and far vision zones is not reduced to such an extent, because the inclination in radial direction of each near vision zones will differ significantly from the inclination in radial direction of circumferentially adjacent far vision zones. However, due to the alternation of far and near vision zones in radial direction, the surface level correction for minimizing steps between radially adjacent far and near vision zones also results in reducing the maximum step between surfaces of circumferentially adjacent near vision and far vision zones. This reduction can amount to reducing the maximum step to at most ⅓ of the maximum step that would be obtained if all near vision zone surfaces are part of one common near vision sphere or asphere and all far vision zone surfaces are part of a common far vision sphere or asphere arranged for minimizing the average step between adjacent near vision and far vision zone surfaces.

Although in the present example the near vision zones 9-11 and the far vision zones 6-8 each occupy approximately 50% of the surface of the optical portion 4, depending on requirements of a user other ratio's between the surface area's of the near vision zones 9-11 and the far vision zones 6-8 may be provided as well. In most cases, it is preferred that the near vision zones form at least 10% and at most 50% of the surface area of the optical portion 4, since good far vision in low light conditions is usually held to be more important than good near vision in low light conditions.

Each zone 6-11 may have an aspheric correction matching the position of that zone in the optical portion 4. In the present example, all zones 6-11 of the anterior surface of the optical portion 4 are aspheric to correct for spherical aberrations, while the posterior surface of the optical portion 4 is of a uniformly spherical shape. It is however also possible to include some or all asphericity in the uniformly shaped surface opposite the surface in which the zones with different refractive powers are formed. Also, the zones with different refractive powers may be provided by shaping such zones partially in the anterior and partially in the posterior surfaces.

The lens 1 has a non-optical portion 18 peripherally bounding the optical portion 4. The non-optical portion 18 supports the optical portion, which is particularly relevant for keeping the optical portion 4 plane if the lens 1 is of the folding type so that also the optical portion 4 is of very flexible material. The non optical portion of the lens body may be of a light absorbing tint, color and/or texture, to avoid optical disturbance by light reflected therefrom.

Within the framework of the invention as set forth in the claims, many other variants are conceivable. For instance, in addition to near and far vision zones, also zones for enhancing vision at intermediate distances may be provided and alternate with the near and far vision zones in circumferential and radial sense. Also, the near and far vision zones may be arranged in an interchanged fashion, so that in any of the embodiments all zones forming near vision zones are replaced by far vision zones and vice versa.

Figure 2:
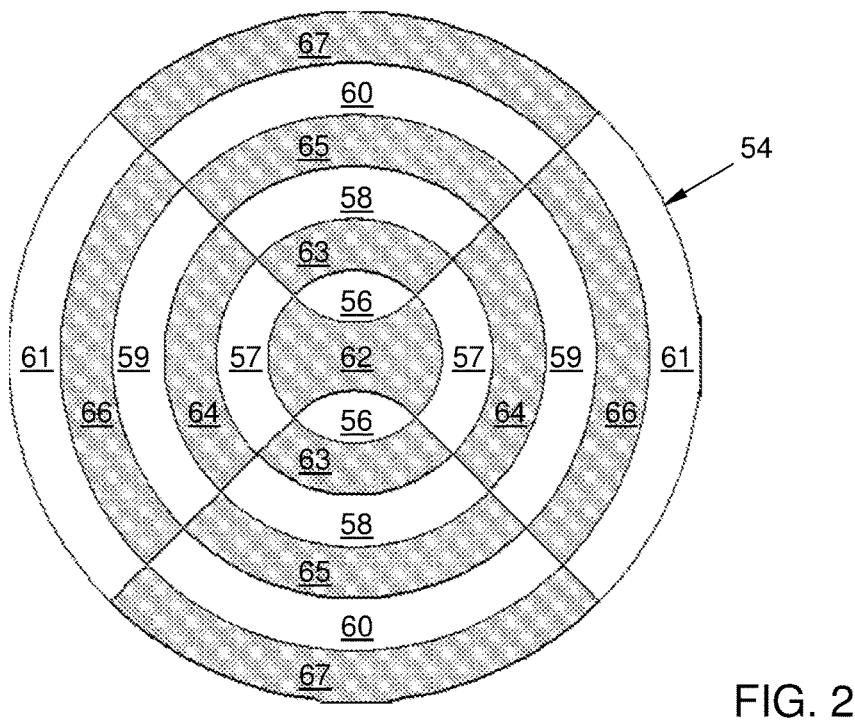
FIG. 2 is a frontal view of an optical portion of a second example of a lens according to the invention.

In FIG. 2, an optical portion 54 of a second example of a lens according to the invention is shown. In this lens, compared with the lens shown in FIG. 1, the number of successive near and far vision zones in radial sense has been increased from two rings of circumferentially alternating near and far vision ring segment zones to five rings of circumferentially alternating near vision ring segment zones 63-67 and far vision ring segment zones 57-61. Within the inner ring of alternating ring segments 57, 63, central far vision ring segment zones 56 and central near vision zone 62 are arranged. The larger the number of rings of circumferentially alternating near and far vision ring segment zones (which may for instance also be three, four or seven of such rings), the smaller the steps between surface levels between in particular circumferentially adjacent near and far vision zones will be. However, with the number of such rings of alternating ring segment zone, the increasing length of borders between adjacent near and far vision zones may offset further advantages gained by the reduced step height.

Figure 3:
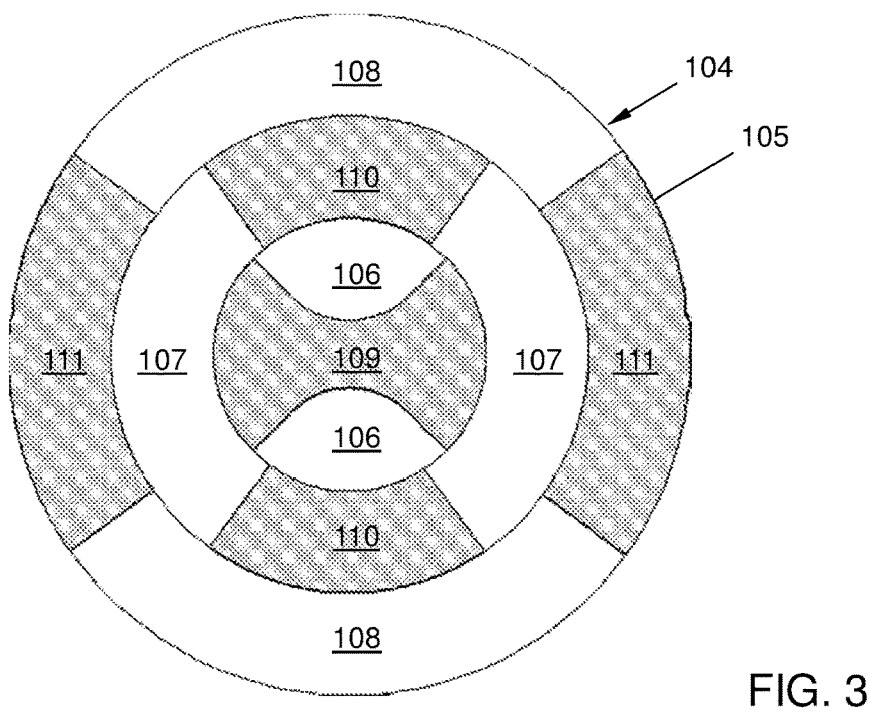
FIG. 3 is a frontal view of an optical portion of a third example of a lens according to the invention.

In FIG. 3, an optical portion 104 of a third example of a lens according to the invention is shown. In this lens, compared with the lens shown in FIG. 1, the size in circumferential sense of the near vision ring segment zones 110, 111 in the rings of circumferentially alternating near and far vision ring segment zones 107, 108, 110, 111 has been reduced, so that the portion of the effective optical surface occupied by the near vision zones 109, 110, 111 reduces as the diameter of the area of the optical portion 104 that is effective increases with the pupil diameter. The pupil diameter tends to increase as ambient light intensity becomes lower. Thus, the proportion of the surface area available for far vision enhancement increases as light levels are lower and far vision becomes more important, for instance when walking in the dark or driving at night.

An increase or decrease of the portion of the effective optical surface occupied by the near vision zones as the diameter of the area of the optical portion that is effective increases with the pupil diameter can also be achieved by arranging borders between radially adjacent far and near vision zones more inwardly or more outwardly.

In the lens according to FIG. 3, borders 133 between circumferentially adjacent far vision zones 108 and near vision zones 111 in the ring bordering the peripheral boundary 105 of the optical portion 104 are not in line with the borders 132 between circumferentially adjacent far vision zones 107 and near vision zones 110 in the ring inwardly bordering on the ring bordering the peripheral boundary 105 of the optical portion 104. These more inward borders 132 are also not in line with the boundary 131 between the most central far vision zones 106 and near vision zone 109. Thus, the lens according to FIG. 3 has more intersections of borders between adjacent vision zones and relatively large steps may occur at the borders between radially adjacent far vision zones 106, 107, 108.

Figure 4:
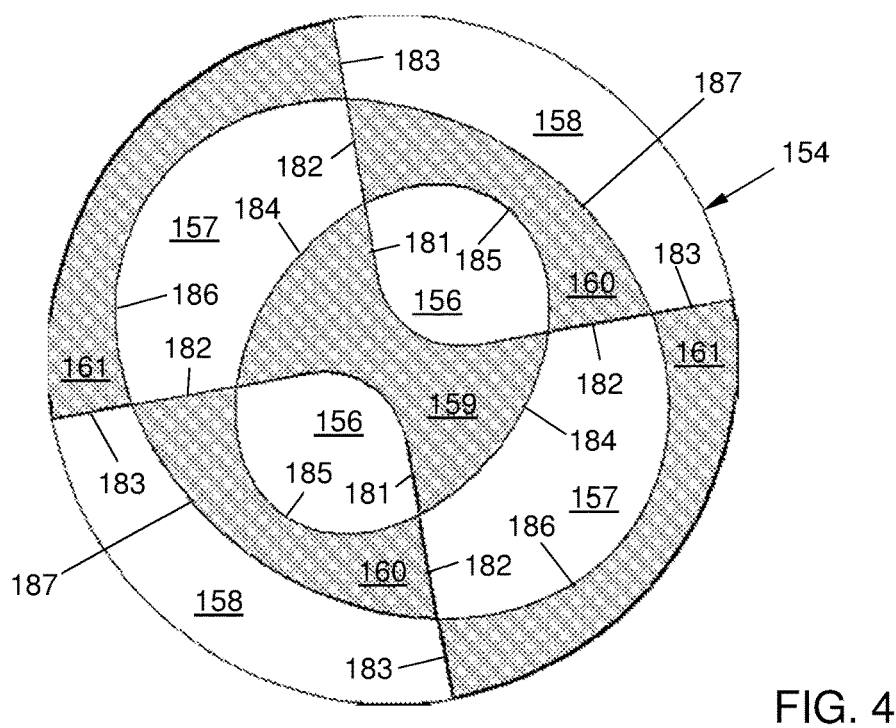
FIG. 4 is a frontal view of an optical portion of a fourth example of a lens according to the invention.

This problem has been solved in the lens according to FIG. 4 in which circumferentially contiguous borders 184-187 between radially successive near vision zones 159-161 and far vision zones 156-158 form non circular shapes, the non circular shapes being arranged such that vision zones of one type (in this example near vision zones 159-161) are smaller in radial direction than vision zones of the other type (in this example far vision zones 156-158). Thus a reduction of the portion of the effective optical surface occupied by the near vision zones 159-161 as the diameter of the area of the optical portion 154 that is effective increases with the pupil diameter, is obtained while maintaining the feature that borders 183 between circumferentially adjacent far vision zones 158 and near vision zones 161 in the ring bordering the peripheral boundary 155 of the optical portion 154 are in line with the borders 182 between circumferentially adjacent far vision zones 157 and near vision zones 160 in the ring inwardly bordering on the ring bordering the peripheral boundary 155 of the optical portion 154. Also the feature that more inward borders 182 are also in line with the borders 181 between the most central far vision zones 156 and near vision zone 109 is maintained. Thus, additional intersections of borders between adjacent vision zones and relatively large steps at the borders between radially adjacent far vision zones are avoided.

The non-circular shapes formed by the circumferentially contiguous borders 184-187 are oval, which is advantageous for keeping the overall length of the borders 184-187 low. A particularly small overall length of these borders 184-187 has been achieved in the present example by providing the non-circular shapes in the form of ellipsoids. For a short overall border length, it is also advantageous that two sets of circumferentially contiguous borders 184, 185 and 186, 187 have been provided, the longitudinal axis of the shape formed by the first set of circumferentially contiguous borders 184, 185 being perpendicular to the longitudinal axis of the shape formed by the other set of circumferentially contiguous borders 186, 187.

Several features have been described as part of the same or separate embodiments. However, it will be appreciated that the scope of the invention also includes embodiments having combinations of all or some of these features other than the specific combinations of features embodied in the examples.

The invention claimed is:

1. An ophthalmic multifocal lens to be worn on or in a human eye, the lens having an optical portion with anterior and posterior surfaces and a circumferential peripheral boundary, the optical portion having far vision zones having a first refractive power and near vision zones having an add power, the far vision zones and near vision zones including ring segments having one of said refractive powers each radially bounding a more central zone of another one of said refractive powers, the ring segments including ring segments bordering on the peripheral boundary and alternating in circumferential sense along the full circumference of the peripheral boundary,
wherein circumferentially contiguous borders between radially successive near vision zones and far vision zones form at least one non-circular shape, the non-circular shape being arranged such that near vision zones or far vision zones of a ring of circumferentially successive ring segment zones are smaller in radial direction than far vision zones or, respectively, near vision zones of the same ring of circumferentially successive ring segment zones.

2. The lens according to claim 1, in which the non-circular shape is an oval shape.

3. An ophthalmic multifocal lens to be worn on or in a human eye, the lens having an optical portion with anterior and posterior surfaces and a circumferential peripheral boundary, the optical portion having far vision zones having a first refractive power and near vision zones having an add power, the far vision zones and near vision zones including ring segments having one of said refractive powers each radially bounding a more central zone of another one of said refractive powers, the ring segments including ring segments bordering on the peripheral boundary and alternating in circumferential sense along the full circumference of the peripheral boundary, wherein:
a first one of a set of circumferentially adjacent ones of said ring segments is of a thickness varying from a first thickness at a radially inner border of said first ring segment to a second thickness at a radially outer border of said first ring segment;
a second one of said set of circumferentially adjacent ones of said ring segments is of a thickness varying from a third thickness at a radially inner border of said second ring segment to a fourth thickness at a radially outer border of said second ring segment;
the first thickness is smaller than the third thickness and the second thickness is larger than the fourth thickness; and
the circumferentially adjacent ring segments of said set are of equal thickness in a position located in radial sense between the inner and outer borders of said set of circumferentially adjacent ring segments.

4. The lens according to claim 3, wherein the ring segments in at least one ring inwardly of said ring segments bordering on the peripheral boundary each bound a radially more central zone along a full inner circumference of said ring.

5. The lens according to claim 3, wherein each far vision one of said ring segments bordering on the circumferential peripheral boundary, radially bounds a near vision ring segment of a ring inwardly of said ring segments bordering on the peripheral boundary and each near vision one of said ring segments bordering on the circumferential peripheral boundary, radially bounds a far vision ring segment of said ring inwardly of said ring segments bordering on the peripheral boundary.

6. The lens according to claim 5, wherein a border between circumferentially neighboring ones of the ring segments bordering on the peripheral boundary is in line with a border between circumferentially neighboring ones of the ring segments of said ring inwardly of said ring segments bordering on the peripheral boundary.

7. The lens according to claim 3, wherein borders between most central ones of the near vision and far vision zones are curved with a convex side facing a center of the optical portion.

8. The lens according to claim 3, wherein the near vision zones form at least 10% and at most 50% of the optical surface area.

9. The lens according to claim 3, in which transition zones between near and far vision zones form at most 5% of the optical surface area.

10. The lens according to claim 3, in which at least one of the ring segments radially bounding a more central zone is flush with the more central zone bounded thereby, in at least one position along a border between said ring segment and said more central zone.

11. The lens according to claim 3, in which each zone has an aspheric correction matching the position of that zone in the optical portion.

12. The lens according to claim 3, further comprising a non-optical portion peripherally bounding the optical portion.

13. The lens according to claim 12, wherein the non-optical portion comprises haptics for suspending the optical portion in an eye.

14. The lens according to claim 3, wherein the circumferential peripheral boundary is of circular or oval shape.

15. The lens according to claim 3, wherein for at least one other set of circumferentially adjacent ones of said ring segments, radially adjacent said set of circumferentially adjacent ones of said ring segments:
a first one of the other set of circumferentially adjacent ones of said ring segments is of a thickness varying from a first thickness at a radially inner border of said other first ring segment to a second thickness at a radially outer border of said other first ring segment;
a second one of said other set of circumferentially adjacent ones of said ring segments is of a thickness varying from a third thickness at a radially inner border of said other second ring segment to a fourth thickness at a radially outer border of said other second ring segment;
the first thickness is smaller than the third thickness and the second thickness is larger than the fourth thickness; and
the circumferentially adjacent ring segments of said other set are of equal thickness in a position located in radial sense between the inner and outer borders of said other set of circumferentially adjacent ring segments.

16. The lens according to claim 3, wherein, for each set of circumferentially adjacent ones of said ring segments:
a first one of a set of circumferentially adjacent ones of said ring segments is of a thickness varying from a first thickness at a radially inner border of said first ring segment to a second thickness at a radially outer border of said first ring segment;
a second one of said set of circumferentially adjacent ones of said ring segments is of a thickness varying from a third thickness at a radially inner border of said second ring segment to a fourth thickness at a radially outer border of said second ring segment;

the first thickness is smaller than the third thickness and the second thickness is larger than the fourth thickness; and the circumferentially adjacent ring segments of said set are of equal thickness in a position located in radial sense between the inner and outer borders of said set of circumferentially adjacent ring segments.

17. The lens according to claim 3, wherein positions of equal thickness of circumferentially adjacent ones of said ring segments are located in a zone between 30 and 70% of the distance between the inner and outer borders of the respective ring segments.

18. The lens according to claim 17, wherein positions of equal thickness of circumferentially adjacent ones of said ring segments are located in a zone between 40 and 60% of the distance between the inner and outer borders of the respective ring segments.

\* \* \* \* \*